United States Patent [19]

Eketorp

[11] Patent Number: 5,229,498
[45] Date of Patent: Jul. 20, 1993

[54] METHOD OF CLEANSING A PROTEIN FROM MULTIVALENT METAL IONS BOUND THERETO

[75] Inventor: Rainer Eketorp, Danderyd, Sweden
[73] Assignee: Kabi Pharmacia AB, Upsala, Sweden
[21] Appl. No.: 778,870
[22] PCT Filed: Jun. 20, 1990
[86] PCT No.: PCT/SE90/00442
  § 371 Date: Dec. 24, 1991
  § 102(e) Date: Dec. 24, 1991
[87] PCT Pub. No.: WO91/00290
  PCT Pub. Date: Jan. 10, 1991

[30] Foreign Application Priority Data
  Jun. 27, 1989 [SE] Sweden .................................. 8902317
[51] Int. Cl.$^5$ .................................................. C07K 3/12
[52] U.S. Cl. ............................... 530/364; 530/387.1; 530/413; 530/414; 530/417; 530/506
[58] Field of Search ................... 530/364, 387.1, 413, 530/414, 417, 506

[56] References Cited

U.S. PATENT DOCUMENTS 4,116,948  9/1978  Mittenzwei et al. ............... 530/417
4,256,631  3/1981  Yokoo et al. ....................... 424/85.8

Primary Examiner—Nathan M. Nutter
Attorney, Agent, or Firm—Pollock, Vande Sande & Priddy

[57] ABSTRACT

A method is provided for cleansing a protein from multivalent metal ions bound thereto, these ions being released from the protein by exchanging the ions with monovalent metal ions, whereafter the multivalent metal ions are removed. The release and removal of these ions is effected, in particular, by diafiltration or gel filtration processes.

20 Claims, 1 Drawing Sheet

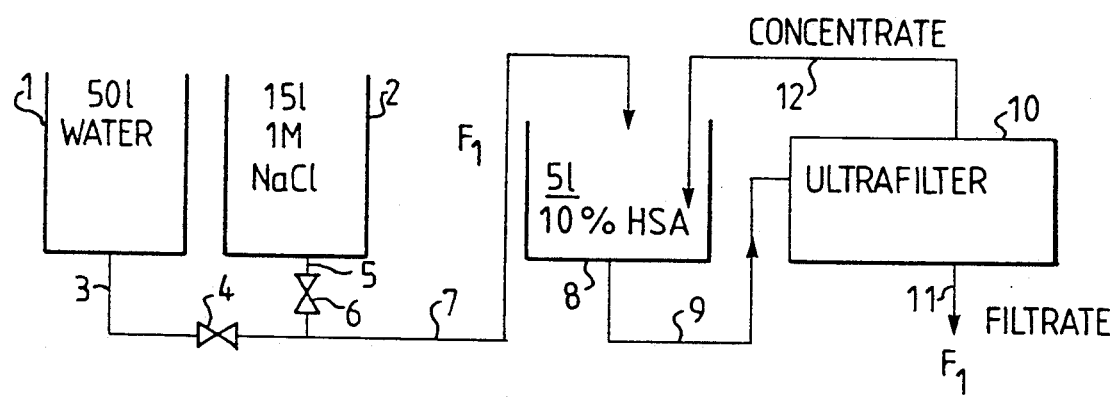

ic products was published in 1986 (May J C Rains T C, Maienthal F J et al.: A survey of the concentrations of eleven metals in vaccins, allergenic extracts, toxoids, blood, blood derivatives, and other biological products. J Biol Stand 1986, 14, 363-375), and it is evident from
METHOD OF CLEANSING A PROTEIN FROM MULTIVALENT METAL IONS BOUND THERETO

TECHNICAL FIELD

The present invention relates to a method of cleansing protein from multivalent metal ions bound thereto.

BACKGROUND ART

Many biologically active proteins have obtained wide use as important drugs. As a result primarily of different cleaning methods, these proteins are liable to contain relatively large quantities of different metals. An investigation into the proportions of metals in various biological products was published in 1986 (May J C Rains T C, Maienthal F J et al.: A survey of the concentrations of eleven metals in vaccins, allergenic extracts, toxoids, blood, blood derivatives, and other biological products. J Biol Stand 1986, 14, 363-375), and it is evident from this investigation that the proportions of metals in, for instance, human serum albumin can reach values which are harmful to patients.

The metals normally derive from the various additives used when working-up and cleansing the proteins. For instance, these processes normally involve the use of filter aids and filters having a relatively high proportion of filter aids for the purpose of clear-filtering solutions in various process stages. These filter aids have often been found to contain metals which are able to bind to the protein in ion form. The problems can be overcome by using other filtering methods, using filters based on inert materials. Such filters, however, are at present particularly expensive in comparison with the filter materials conventionally used.

In the case of many proteins, multivalent metal ions are bound strongly to the protein, probably due to chelate formation and ion-exchange effects.

Endeavours have also been made to remove the bound metals ions by treatment with various complex formers, such as EDTA or citrate ions. The metal ions, however, are bound so strongly to the proteins that these endeavours have met with no success.

The contaminating multivalent metal ions in the proteins may, for instance, consist of one or more of the metals aluminium, chromium, lead, mercury, iron, nickel, copper and magnesium. Of these metal ions, the removal of aluminium, iron and lead is the most important.

Aluminium, which is the most common metal in the earth's crust has been assumed to constitute an ethiological factor in a number of clinical illness conditions, such as senile demens of the Alzheimer type (Crapper D. R, Kishnan S S, Quittat S. Aluminium, neurofibrillary degeneration and Alzheimer's disease. Brian 1976, 99, 67-80; and Crapper D R, Quittat S, Krishnan S S et al.: Intranuclear aluminium content in Alzheimer's disease, dialysis encephalo-Acta Neuropath 1980, 50, 19-24) and dialysis encephalopath (Alfrey A C, Le Gendre G R, Kaehny W D: The dialysis encephalopathy syndrome. Possible aluminium intoxication. N Eng. Med 1976, 294 184-188;

Alfrey A C, Hegg A, Craswell P: Metabolism and toxicity of aluminium in renal failure. Am J Clin Nutr 1980, 33, 1509-1516; and Per D P, Gajdusek D C, Garruto R M et al.: Intraneuronal aluminium accumulation in amyothropic lateral sclerosis and Parkinson-dementia of Guam. Science 1982, 217, 1053-1055), etc. It has been clearly established that aluminium is accumulated in the tissues and has a toxic effect on patients suffering from kidney function disorders.

The injurous effect of other metals, such as iron, chromium, nickel and lead, is previously known, either due to their normal toxicity, or due to their ability to promote allergies, for instance.

SUMMARY OF INVENTION

The aforesaid disadvantages are avoided by the present invention, which provides a method of cleansing proteins of the multivalent metal ions bound thereto, so as to obtain as the end product one or more proteins in which the proportion of strongly bound multivalent metal ions is greatly reduced.

In accordance with the present invention, a protein is cleansed of multivalent metal ions bound thereto by releasing the multivalent metal ions by exchanging said multivalent ions with monovalent metal ions and removing the replaced multivalent metal ions. In accordance with one particular embodiment of the invention, the monovalent metal ions are subsequently also removed.

The monovalent metal ions used to substitute the multivalent metal ions are primarily alkali metal cations, and then particularly sodium or potassium, or ammonium cations.

BRIEF DESCRIPTION OF THE DRAWING

The accompanying drawing is a flow sheet of a diafiltration process, which constitutes one embodiment of the invention and which is described in more detail in the following examples.

BEST AND VARIOUS MODES FOR CARRYING OUT INVENTION

The multivalent metal ions bound to the protein are exchanged with the monovalent metal ions, by treating a solution of the protein with a solution of a salt of a monovalent metal ion in high concentration. This process displaces the equilibrium, so that the multivalent cations are displaced by the monovalent cations. The released multivalent metal cations can then be removed with the aid of one or several known processes. Processes found particularly operable in both exchange stages are diafiltration and gel filtration.

In the case of diafiltration, the liquid to be filtered is caused to flow parallel with the surface of the filter and a pressure gradient is applied over the filter. The pore size of the filter is selected in correspondence with the molecular size of the protein to be cleansed, so that the protein molecules are retained while the metal ions pass through the filter. The size of the pores is normally of the order of nanometers. A solution of salt of monovalent metal ions in high concentration is added to the protein solution, before passing the solution over the filter surface. This causes the bound multivalent metal ions to be displaced from the protein and substituted by monovalent metal ions, and the multivalent metal ions will then pass through the filter as filtrate. A further solution of monovalent metal salt in a quantity corresponding to the withdrawn filtrate is then added to the resultant protein-solution concentrate, and the solution is recycled for further filtration, this process being continued until the content of multivalent metal ions has been reduced to the desired value.

If desired, the diafiltration process can then be continued with the addition of water instead of salt solution, the monovalent metal ions being displaced from the protein molecules and removed through the filter.

The same principles can be applied in gel filtration, using some known gel filtration material, e.g. a cross-linked dextran gel, such as Sephadex ® G 10 or G 25. The gel filter material is selected so as to have an appropriate pore size commensurate with the molecular size of the protein to be cleansed. The gel filtration process is carried out with the protein in a buffer solution containing a high proportion of monovalent metal salt, in order to displace the bound multivalent metal ions. The desired cleansing effect can be achieved, in the majority of cases, by adding a sufficient quantity of monovalent metal salt to the sample to be gel-filtered. When the pore size of the gel-filter material is correctly adapted, the protein will flow through the filter medium while the multivalent metal ions will be delayed, thereby enabling said multivalent metal ions to be isolated from the protein. The proportion of monovalent metal salt in the solution used to displace the multivalent metal ions from the protein in the diafiltration or gel filtration process can vary within relatively wide limits. The absolute lowest limit of this range is determined by the physiological salt content, thus 0.9% w/v or 0.15 M. The upper limit is decided, in principle, by the saturation content of the salt concerned in the solution, although other factors may also have significance. For instance, some proteins can be denatured by high salt contents. The person skilled in this art, however, will have no difficulty in finding an operable salt content on the basis of simple experiments.

Particularly different types of proteins can be cleansed by means of the inventive method. The method has been found particularly expedient for cleansing albumin, such as human serum albumin, and gammaglobulin. The invention is not restricted, however, to the cleansing of solely these proteins.

The invention will now be further illustrated with reference to the following examples.

EXAMPLE 1

5 l of a 10-percent solution of human serum albumin (HSA) was diafiltered against 15 l of a 1 M sodium chloride solution. Apparatus for carrying out the method are shown schematically in the accompanying drawing.

The apparatus include a water storage tank 1 and a supply tank 2 for 1 M sodium chloride solution. The storage tanks are connected to a common conduit 7 which leads to a storage container 8 for albumin solution, via outlet pipes 3 and 5 and valves 4 and 6 respectively. The albumin solution is passed from the container 8 through a pipe 9 and into an ultra-filtering device 10, the filter of which has a porosity of 10 000 ("cut off" molecular weight). A filtrate is removed from the filter device 10 through a pipe 11 and a concentrate is recirculated through a pipe 12 to the storage vessel 8. The removed filtrate has a volume of $F_1$, and an equally large volume $F_1$ of water or salt solution is passed to the storage vessel 8, through the pipe 7, so as to hold the volume constant.

During the filtration process, the valve 4 is closed and the valve 6 open at first, and salt solution is passed from the storage tank 2 to the storage container 8, so as to displace the multivalent metal ions from the protein, these multivalent metal ions then being removed in the filtrate, through the pipe 11. When the filtration process has continued over a length of time such that the proportion of multivalent metal ions in the protein has been reduced to the desired value, the valve 6 is closed and the valve 4 opened, and the filtration process is continued with the addition of clean water, so as to, in turn, displace the monovalent metal ions from the protein and remove said monovalent ions in the filtrate, through the pipe 11. Filtration with the addition of clean water is then continued until the proportion of monovalent metal ions has decreased to the desired value.

In the illustrated example, 15 l M sodium chloride solution is added continuously to the albumin solution during the filtering process, wherewith the proportion of multivalent metal ions in the albumin solution, e.g. aluminium, is reduced to a value beneath 30 $\mu$g/l. The input values of the metal content normally lie within the range of 200 to 1500 $\mu$g/l. The reduction of the proportion of undesirable multivalent metal ions in the protein is thus very considerable.

The proportions of Fe, Pb and Cr in the input albumin solution were 3.2, 0.36 and 0.6 mg/l respectively. Subsequent to treatment, these proportions were found to have reduced to 0.3, 0.08 and 0.02 mg/ml respectively.

EXAMPLE 2

Crude albumin from ethanol fractionation of plasma (Fr. V) was dissolved to a content of about 10% in distilled water. The solution was filtered and the pH adjusted to 7.0.

Diafiltration was then effected against a sodium chloride solution, containing 2 mol/l NaCl. 135 l of this solution was used in total. For each 45 liters added, samples were taken for determining the aluminium content Ultrafilters having a "cut off" of 10 000 were used. The results are set forth in the following Table 1:

TABLE 1

| Diafiltration solution added | Al-content mg/l |
|---|---|
| 0 | 0.35 |
| 45 | 0.16 |
| 90 | 0.11 |
| 135 | 0.04 |

Subsequent to reducing the sodium content, the aluminium content was found to be 0.01 mg/l.

EXAMPLE 3

Crude albumin according to Example 2 was dissolved in distilled water to a proportion of about 10%. The solution was filtered and the pH of the filtrate adjusted to 7.0. The total volume was 3 liters. Solid sodium chloride was added to the solution, to a proportion of 2 mol/l, and the aluminium proportion of the solution was assayed as being 0.86 mg/ml. The solution was then diafiltered against 9 liters of NaCl-solution having a proportion of 2 mol/l. The diafilter used had a "cut off" at molecular weight 10 000. The aluminium proportions of the albumin solution and the permeate was assayed, after addition of given quantities of NaCl-solution. The results are set forth in the following Table 2.

TABLE 2

| Volume diafiltered solution, l | Albumin solution Al-cont. mg/ml | Permeate Al-cont. mg/ml |
|---|---|---|
| 1.5 | 0.41 | 0.56 |
| 3 | 0.32 | 0.31 |
| 4.5 | 0.23 | 0.24 |

TABLE 2-continued

| Volume diafiltered solution, l | Albumin solution Al-cont. mg/ml | Permeate Al-cont. mg/ml |
|---|---|---|
| 6 | 0.16 | 0.16 |
| 9 | 0.09 | 0.10 |

The albumin solution was then diafiltered against 30 liters of distilled water for de-salting purposes, and the aluminium content of the solution was determined during the de-salting process. The results are set forth in the following Table 3:

TABLE 3

| Volume, l | Albumin solution Al-cont, mg/ml |
|---|---|
| 2 | 0.02 |
| 4 | <0.01 |
| 6 | <0.01 |
| 8 | <0.01 |
| 10 | <0.01 |

The solution was concentrated to an albumin content of 20%, after the de-salting process, whereafter the aluminium content was measured to 0.02 mg/ml.

EXAMPLE 4

41.4 kg of a 10-percent albumin solution was pH-adjusted to 7.0, and sodium chloride in solid form was added to a content of 2 mol/l. A sample of the solution was analyzed with respect to its contents of Al, Fe, Cr and Mg.

The solution was diafiltered with 125 liters of sodium chloride solution having the content of 2 mol/l. The solution was then de-salted with distilled water until the sodium content was less than 0.7 mg/ml. This level was reached after adding 250 liters of distilled water.

After de-salting the solution, the solution was concentrated to an albumin content of 20% and sterile filtered and introduced into bottles (100 ml) for heat treatment at 60° C. for 10 hours. The proportions in which the aforesaid metal were present in the solution were determined prior to the de-salting process and after heat-treating the bottles, the analysis results obtained being set forth in the following Table 4.

TABLE 4

| | mg/l | | | |
|---|---|---|---|---|
| | Al | Fe | Cr | Mg |
| Starting material calculated to 20% albumin | 0.47 | 4.34 | 0.08 | 2.51 |
| Concentrate from diafiltration | 0.02 | 0.7 | 0.03 | 0.1 |
| In bottles after heat treatment | 0.02 | 0.3 | <0.01 | 0.1 |

The present invention thus provides a simple and convenient method of removing undesirable multivalent metal ions bound to a protein. The method can be applied generally for cleansing proteins and is not restricted solely to the examples described in this document. It will also be seen that further variants and modifications of the invention are possible within the scope of the following claims. For instance, the proteins can be cleansed by ultrafiltration, although this method is not as rational as the described method, since it is then necessary to add further salt solution or water. The inventive principles remain unchanged, however.

I claim:

1. A method of cleansing a protein from multivalent metal ions bound thereto, characterized in that the multivalent metal ions are released from the protein by substituting them with monovalent alkali metal ions or ammonium ions, by subjecting the protein with multivalent metal ions bound thereto to a diafiltration process against an aqueous solution which contains the monovalent alkali metal ions or ammonium ions in a concentration from about 0.15 M up to saturation, such that said multivalent metal ions are displaced from the protein and are obtained in a filtrate, or by subjecting the protein with multivalent metal ions bound thereto to a gel filtration in an aqueous solution of the monovalent alkali metal ions or ammonium ions in a concentration from about 0.15 M up to saturation, such that the multivalent metal ions are displaced from the protein and are delayed in the filtration, and then removing the multivalent metal ions that have been released from the protein.

2. A method according to claim 1, characterized in that after the substitution of the multivalent metal ions with the monovalent alkali metal ions or ammonium ions, said monovalent metal ions are removed from the protein by subjecting said protein to a renewed diafiltration against a solution which essentially does not contain any metal ions, or by subjecting said protein to a renewed gel filtration in a solution which essentially does not contain any metal ions.

3. A method according to claim 1 characterized in that said multivalent metal ions are selected from the group consisting of aluminium, iron and mixtures thereof.

4. A method according to claim 1, characterized in that said monovalent metal ions are selected from the group consisting of sodium and potassium ions.

5. A method according to claim 1, characterized in that the protein is selected from the group consisting of albumin and gamma globulin.

6. A method according to claim 1, characterized in that the protein is albumin, and the multivalent metal ion is aluminum.

7. The method of claim 1 wherein ammonium ions are employed.

8. The method of claim 1 which comprises subjecting said protein with multivalent metal ions bound thereto to said diafiltration process.

9. The method of claim 1 which comprises subjecting said protein with multivalent metal ions bound thereto to said gel filtration.

10. The method of claim 1 wherein after the substitution of said multivalent metal ions with said monovalent alkali metal ions or ammonium ions, said monovalent metal ions are removed from the protein by subjecting said protein to a renewed diafiltration against a solution which essentially does not contain any metal ions.

11. The method of claim 10 wherein said multivalent metal ions are selected from the group consisting of aluminum, iron, lead and mixtures thereof.

12. The method of claim 10 wherein said monovalent metal ions are selected from the group consisting of sodium and potassium ions.

13. The method of claim 10 wherein ammonium ions are employed.

14. The method of claim 10 wherein said protein is selected from the group consisting of albumin and gamma globulin.

15. The method of claim 1 wherein after the substitution of said multivalent metal ions with said monovalent alkali metal ions or ammonium ions, said monovalent metal ions are removed from the protein by subjecting said protein to a renewed gel filtration in a solution which essentially does not contain any metal ions.

16. The method of claim 15 wherein said multivalent metal ions are selected from the group consisting of aluminum, iron, lead and mixtures thereof.

17. The method of claim 15 wherein said monovalent metal ions are selected from the group consisting of sodium and potassium ions.

18. The method of claim 15 wherein said protein is selected from the group consisting of albumin and gamma globulin.

19. The method of claim 15 wherein ammonium ions are employed.

20. The method of claim 2 wherein the protein is albumin and the multivalent metal is aluminum.

* * * * *